United States Patent [19]
Gerth et al.

[11] Patent Number: 5,925,377
[45] Date of Patent: Jul. 20, 1999

[54] DIETARY SUPPLEMENT COMPOSITION

[75] Inventors: Teja D. Gerth, Los Angeles; Ralph W. Mann, Canyon Lake; James R. Ayres, Menifee, all of Calif.

[73] Assignee: Nova Pharmaceutical Co., Lake Elsinore, Calif.

[21] Appl. No.: 08/910,971

[22] Filed: Aug. 7, 1997

[51] Int. Cl.$^6$ ........................................................ A61K 9/48
[52] U.S. Cl. ......................... 424/451; 424/464; 424/484; 424/400
[58] Field of Search .................................. 424/451, 464, 424/484, 400

[56] References Cited

U.S. PATENT DOCUMENTS 5,273,754  12/1993  Mann ........................................ 424/440
5,635,535   6/1997  Wagstaff .................................. 514/557

*Primary Examiner*—Jose' G. Dees
*Assistant Examiner*—Michael A. Williamson
*Attorney, Agent, or Firm*—Blakely, Sokoloff, Taylor & Zafman, LLP

[57] ABSTRACT

A dietary supplement composition combining amino acids, minerals, vitamins, herbs, and essential nutrients along with gentle diuretics and digestive enzymes. Together, the individual elements of the composition work in a synergistic manner to promote the benefits of the individual elements. For example, DL-phenylalanine is combined with tyrosine to act as an appetite depressant while L-carnitine is combined with chromium picolinate to work as fat directors to convert stored body fat into energy.

15 Claims, No Drawings

DIETARY SUPPLEMENT COMPOSITION

BACKGROUND OF THE INVENTION

1. Field of the Invention

The invention relates to dietary supplements and more particularly to a dietary supplement composition.

2. Description of Related Art

There are many dietary supplements on the market that promote general health. These supplements typically take the form of tablets, capsules, or liquids that are combined with meals as part of a healthy diet regimen. These supplements are made up individually of one or more amino acids, minerals, and/or nutrients.

Certain amino acids burn fat, reduce hunger, and act as anti-depressants. Amino acid compounds, for example, DL-Phenylalanine and L-Tyrosine are high ranking neurotransmitter amino acids that stimulate and modify brain activity to reduce hunger and improve memory and mental alertness. L-Glutamine is a natural form of glutamic acid that helps decrease sugar cravings. As this amino acid helps those with a "sweet tooth," it also helps fight fatigue and depression.

Vitamins are vital elements to obtain a proper metabolism. The vitamin B family, for example, helps the body and mind in many ways. For example, vitamin B12 and vitamin B6 regenerate red blood cells. Vitamin B1 improves mental attitude, and keeps the nervous system, muscles, and heart functioning normally. Vitamin B2 plays a role in cosmetic care by promoting healthy skin, nails and hair. Niacin is a member of the B-complex family. Niacin promotes a healthy digestive system, reduces high blood pressure, and increases energy through proper utilization of food.

Minerals enhance the activity of both amino acids and vitamins, while providing essential nutrients. Calcium, for example, helps keep the heart beating regularly, alleviates insomnia, and helps metabolize the body's iron. Magnesium alleviates stress and plays an important role in converting blood sugar into energy. Further, calcium and magnesium work together for cardiovascular health. Zinc is essential for protein synthesis, and governs the contractibility of muscles and is important for food stability.

Apart from dietary supplements that are designed to promote general health, there are also dietary products on the market directed at weight loss. These products generally concern efforts to suppress the appetite. Most weight loss products utilize caffeine or artificial stimulants, as well as sugars or mahuang (ephedra) that act as stimulants to give a short-lived anti-depressant and appetite depressant or suppressant effect. While these products may depress appetite cravings, the stimulants promote anxiety and nervousness and raise the heart rate in many individuals. These products may be effective for a short time by reducing food intake, but ultimately users of these products return to their former eating habits.

SUMMARY OF THE INVENTION

A dietary supplement composition combining amino acids, minerals, vitamins, herbs, and essential nutrients along with gentle diuretics and digestive enzymes is disclosed. The supplement provides a 100% natural weight loss aid that suppresses appetite and burns fat, while providing minerals, vitamins, and other essential nutrients that the body needs.

The combination of particular elements yields a composition directed particularly at weight loss, that contains elements that depend on each other to increase or enhance an individual element's effectiveness. For example, DL-phenylalanine is converted into tyrosine to act as an appetite suppressant. The inclusion of St. John's Wort, a natural anti-depressant agent, alleviates any anxiety triggered by the appetite suppressants. St. John's Wort also acts as an appetite suppressant. L-carnitine and chromium picolinate, other elements of one embodiment of the supplement composition, work as fat directors by converting stored body fat into energy. The amino acid components supply or convert to the important amino acids the body needs daily. Similarly, the minerals supply the body with electrolytes and micro-nutrients the body might not otherwise receive when dieting. One embodiment of the supplement composition further includes gentle diuretics and digestive enzymes to assure comfortable and easy digestion. Thus, the elements of the dietary supplement of the invention use synergism for maximum results. The composition treats weight loss, mental health/well-being, and physical health together to maximize results.

Additional features and benefits of the invention will become apparent from the detailed description, and claims set forth below.

DETAILED DESCRIPTION OF THE INVENTION

Embodiments in accordance with the invention include dietary supplements that are particularly useful in nutrition and weight loss. In the following description, numerous specific details are set forth such as specific formulations, processing steps, process parameters, etc., in order to provide a thorough understanding of the invention. One skilled in the art will understand that these specific details need not be employed to practice the invention.

The invention relates to a dietary supplement composition combining, in one embodiment, amino acids, minerals, vitamins, herbs, and essential nutrients together with gentle diuretics and digestive enzymes. The composition is developed particularly for persons who desire to lose 10–200 pounds, while maintaining the essential nutritional requirements of vitamins, minerals, and nutrients.

Studies reveal that cellular deficiencies affect a network of functions in the human body. Overeating can be attributed to these "network" deficiencies. To effectively treat overeating requires a number of essential compounds and elements. The composition of the invention supplies the full range of these needed compounds. The amino acid components supply or convert to many of the amino acids required daily. The enzymes in the composition promote proper gastrointestinal digestion and absorption of food, while the vitamins maintain and induce metabolism. The minerals in the composition maintain electrolytes and the micro-nutrients as well as other ingredients act as neurotransmitters between the hypothalamus and the central nervous system which regulate all the body's autonomous functions including hunger.

The network deficiencies of amino acids, enzymes, vitamins, minerals, and other essential nutrients recognized by this inventor are so common that a majority of people in the general population are probably deficient to some degree. It therefore is not surprising that a significant portion of the U.S. population is overweight, and that their efforts to control their weight through conventional dieting or medical treatments are often unsuccessful.

The active ingredients in one embodiment are (1) amino acids: DL-phenylalanine, L-glutamine, L-tyrosine, and L-carnitine, in an amount of 50–65 percent by weight of the total composition; (2) herbs: St. John's Wort, in an amount of 10–20 percent by weight of the total composition; and (3) vitamins and minerals: Vitamin B6 and chromium picolinate, in an amount of less than one percent to 15 percent by weight of the total composition. Gentle diuretics and digestive enzymes can be added in an amount of 10–15 percent by weight of the total composition to promote digestion of carbohydrates and proteins.

Example I presents one embodiment of the composition of the invention.

EXAMPLE I

|  |  | % by weight |
|---|---|---|
| DL-PHENYLALANINE | 300 mg | 38.02 |
| L-GLUTAMINE | 50 mg | 6.33 |
| L-TYROSINE | 100 mg | 13.00 |
| ST. JOHN'S WORT EXT. | 50 mg | 6.33 |
| L-CARNITINE | 20 mg | 3.00 |
| CHROMIUM PICOLINATE | 0.6 | <1 |
| KOREAN GINSENG | 70 mg | 9.00 |
| PEPSIN | 15 mg | 1.90 |
| BROMELAIN | 25 mg | 3.18 |
| UVA URSI | 50 mg | 7.00 |
| VITAMIN B-1 (THIAMIN HC 1) | 4 mg | 0.05 |
| VITAMIN B-2 (RIBOFLAV) | 4 mg | 0.05 |
| VITAMIN B-3 (NIACIN) | 10 mg | 1.27 |
| VITAMIN B-6 (PYRIDOXINE) | 4 mg | 0.05 |
| VITAMIN B-12 (CYANOCOBALAMIN) | 0.166 mg | <1 |
| MAGNESIUM (MAGNESIUM OXIDE) | 2 mg | 0.03 |
| ZINC (ZINC OXIDE) | 2 mg | 0.03 |
| CALCIUM (CALCIUM CARBONATE) | 83 mg | 11.00 |
|  | 789.766 | 100.24 |

The above embodiment describes the composition for a single serving size. The composition may be in any convenient dietary supplement form. Examples include capsules, wherein, for example, a serving size is two capsules. To make capsules, the above components are mixed with food stuffs or an inert carrier (e.g., starch or calcium carbonate or lactose) in a conventional manner as known in the art. It is to be appreciated that other suitable forms, such as powder or liquid, prepared in conventional manners, with or without food stuff or inert carriers, are also contemplated.

The contribution of the individual components is described.

DL-phenylalanine (DLPA) is an essential amino acid that is a neurotransmitter. Some of DLPA's main functions are hunger reduction, improvements in memory and mental alertness, and depression alleviation. DLPA also has the ability to convert into most of the other 14 vital amino acids necessary to form proteins required for cellular DNA.

L-glutamine is a natural form of glutamic acid that decreases sugar cravings, fatigue, and depression. L-tyrosine is a high ranking neurotransmitter with an important role in stimulating and modifying brain activity. Clinical studies have shown that tyrosine supplementation also controls depression and anxiety.

L-carnitine is an amino acid-like structure that plays an important role in converting stored body fat into energy. L-carnitine also helps control hypoglycemia and reduces angina attacks.

L-tyrosine is a neurotransmitter that stimulates and modifies brain activity that supplies the precursor for the thyroid gland. Clinical studies show that L-tyrosine helps control depression and anxiety.

St. John's Wort is an herb with many known health benefits. Medicinal treatments with this herb date back to the middle ages. Through the years, St. John's Wort has been used as treatment for anxiety and insomnia. St. John's Wort can help alleviate depression (depressive eaters) and anxiety, alleviates insomnia, helps the body fight viral infection, and promotes healing. St. John's Wort also reduces feelings of hunger and thus acts as a natural appetite suppressant.

Korean ginseng is a natural medicinal herb that is used to stimulate mental and physical energy and to regulate blood pressure.

Chromium picolinate is an essential mineral that works with insulin in the metabolism of sugar. Chromium picolinate stores proteins properly in order to burn fat. Chromium picolinate prevents and lowers high blood pressure and works as a deterrent for diabetes.

Pepsin is a digestive enzyme that breaks up the proteins of ingested food, splitting them into usable amino acids. Without pepsin, protein could not be used to build healthy skin, strong skeletal structure, rich blood supply, or strong muscles.

Bromelain is an enzyme that specializes in proper digestion of proteins and carbohydrates. Bromelain aids in lowering cholesterol levels.

Uva ursi (bearberry) is an herb that acts as an excellent diuretic. The herb is also effective for treatment of bladder and kidney ailments. Uva ursi can further eliminate bloating due to water retention and relieve pain from cystitis and nephritis.

Vitamin B6 is used in the production of antibodies and red blood cells. This vitamin properly assimilates protein and fat, and can also help prevent various nervous and skin disorders.

Vitamin B12 (cobalamin) is known as the "Red Vitamin." Vitamin B12 is the only vitamin that contains essential mineral elements. Vitamin B12 forms and regenerates red blood cells, promotes growth, increases energy, properly utilizes fats, carbohydrates and protein, helps relieve irritability, and improves concentration, memory and balance.

Vitamin B1 (thiamin) helps promote growth, aid digestion (especially of carbohydrates), improve mental attitude, and keep nervous system, muscles, and heart functioning normally. Vitamin B2 (riboflavin) aids in growth and reproduction, and promotes elf healthy skin, nails and hair.

Niacin is a member of the B-complex family, also known as Vitamin B3. Niacin aids in promoting a healthy digestive system, healthier-looking skin, increased circulation, reduced high blood pressure, and increased energy through proper utilization of food.

The body secretes any excess B-complex vitamins and thus does not store the same in the body. B-complex vitamins, particularly those described above, must be replaced daily to maintain good health. The embodiment of Example I provides this replacement.

Magnesium is an anti-stress mineral. Magnesium plays an important role in converting blood sugar into energy. Magnesium can aid in fighting depression, promote a healthier cardiovascular system, keep teeth healthier, and help prevent calcium deposits, kidney stones and gallstones.

Zinc is a micro-nutrient. Zinc is essential for protein synthesis, governs the contractibility of muscles, helps in the formation of insulin, and is important for food stability and in maintaining the body's acid-alkaline balance.

There is more calcium in the body than any other mineral. Calcium and magnesium work together for cardiovascular health. Calcium itself helps to maintain strong bones and healthy teeth. Calcium promotes a regular heart beat, alleviates insomnia, and helps metabolize the body's iron.

The composition according to one embodiment of the invention uses "teamwork" or synergism for maximum results in weight loss, mental health/well-being, and physical health. The teamwork or synergism produces results that were heretofore unachievable with the weight loss supplements in the prior art. This is because the prior art supplements used only one component to address one area (e.g., weight loss) and did not consider how to maximize results or how treatment of the one area would effect other areas (e.g., well-being, physical health). The composition of the invention, on the other hand, views weight loss, mental health/well-being, and physical health as a complete package and recognizes that changes in one area effect other areas.

For weight loss purposes, DL-phenylalanine and L-tyrosine and the herb St. John's Wort work in conjunction in one embodiment to act as an appetite suppressant. In order to function as an appetite suppressant, DL-phenylalanine particularly must be phenylalanine converted into tyrosine. Tyrosine is an amino acid that is a high-ranking neurotransmitter that stimulates brain activity. L-glutamine is a natural form of glutamic acid that decreases sugar cravings. By combining L-glutamine in a supplement with DL-phenylalanine and L-tyrosine, the appetite is suppressed by the function of L-tyrosine and sugar cravings are decreased by L-glutamine. L-glutamine further helps fight fatigue and depression symptoms often associated with weight loss efforts. St. John's Wort also serves as a natural anti-depressant to relieve any anxiety or insomnia brought on by the appetite suppressants.

The body fat burning powers of the composition are concentrated in the elements of L-carnitine and chromium picolinate. L-carnitine converts stored body fat into energy and chromium picolinate stores proteins properly in order to burn fat. Combining the two together increases the amount of fat conversion taking place with the composition as opposed to either of these elements used individually in conventional supplements. Further, L-carnitine and chromium picolinate also help lower high blood pressure, reduce angina attacks and act as a deterrent for diabetes.

Thus, the above composition describes an embodiment of the composition of the invention that depresses the appetite and sugar cravings, activates enzymes and other agents necessary to metabolize fat, and converts stored body fat into energy. Combining the above components with essential vitamins and minerals aids in establishing a proper metabolism, essential vitamins and minerals an individual might otherwise ignore when taking appetite suppressants. Thus, the essential vitamins and minerals of the composition of the invention enhance the activity of the amino acids and vitamins, and provides essential nutrients. Adding specific amounts of diuretics and digestive enzymes (e.g., pepsin, bromelain, and uva ursi) promotes proper digestion of proteins and carbohydrates. The diuretics and digestive enzymes also aid in lowering cholesterol levels, preventing bladder and kidney ailments, and eliminating bloating due to water retention. Pepsin, for example, plays a further important role by enhancing usable amino acids by splitting proteins of ingested foods.

Thus, for the first time, a composition according to one embodiment of the invention has been developed that combines amino acids, vitamins, minerals, essential nutrients, diuretics, and digestive enzymes for ultimate weight loss, metabolic performance, mental health/well-being, and physical health.

Clinical Study

A 90-day, double-blind retrospective study was conducted to investigate the effect of the composition of the invention on weight loss as part of a weight loss program that also included diet control and exercise. The composition of the invention was compared to the effects of a placebo consisting of a brand-name multi-vitamin.

A test panel was selected of 42 individuals, 32 women and 10 men, who were an average of 60 pounds overweight. The individuals were divided into two groups. Group I consisted of 22 members (17 females and 5 males) and received 6 placebo capsules daily. Group II consisted of 20 members (15 females and 5 males) and received 6 capsules of the composition of the invention daily. Both groups received 3 daily doses of 2 capsules each, taken 30 minutes before meals.

Patients in both groups were given identical counseling each week to follow a program of exercise and nutrition. Each patient was instructed to increase their current level of exercise by an additional 30 minutes daily. All patients were provided with dietary calendars and asked to record their daily intake of foods and liquids. Consultations were held weekly between patients and a physician or other medical professional. Patients were encouraged to discuss their weight loss program, including successes, difficulties, or topics of concern to them. During these weekly consultations, patients were weighed and measurements were taken to record blood pressure, pulse rate and respiration. Patients were asked to report their energy levels, exercise activity, cravings for sugar and carbohydrates, any changes in appetite, and any possible side effects of the course of treatment.

Weight loss was measured and recorded in three ways: (1) Total weight loss from the patient's initial weight; (2) reduction in excess weight; and (3) percentage of the excess weight that was lost.

Each 2-capsule dose of the tested embodiment of the invention consisted of: 300 mg DL-Phenylalanine; 50 mg L-Glutamine; 100 mg L-Tyrosine; 50 mg St. John's Wort; 20 L-Carnitine; 600 mcg Chromium Picolinate; 4 mg Vitamin B6; 70 mg Korean Ginseng; 15 mg Pepsin; 25 mg Bromelain; 50 mg Uva Ursi; 4 mg Vitamin B1 (Thiamine); 4 mg Vitamin B2 (riboflavin); 10 mg Vitamin B3 (niacin); 166 mcg Vitamin B12 (Cyanocobalamin); 2 mg Magnesium (Oxide); 2 mg Zinc(Oxide); 83 mg Calcium(Carbonate).

The test panel using the composition of the invention had a 73% success rate in complying with the prescribed diet. The test panel given the vitamin placebo had a 27% success rate in complying with the prescribed diet.

Panelists of Group I taking the multi-vitamin reported no side effects. The only side effect reported by some members of Group II was a dryness in the mouth which dissipated within 5–7 days for all effected patients.

Members of Group I taking the multi-vitamin lost an average of 10 pounds per person over the course of the 90 day trial. This weight loss can be attributed to the diet and exercise program as well as the placebo effect of the capsules. Members of Group II lost an average of 27 pounds, or 2.7 times the amount lost by the control group. Members of Group II lost an average of 45% of their excess weight, compared to 17% of excess weight lost by members of Group I. The study showed no significant differences between male and female subjects in their amount or percentage of weight loss. Further, the study showed no significant differences between patients who ate more and exercised more, compared to those who ate less and exercised less. Finally, members of Group II reported significantly increased levels of energy and stamina. Members of Group I reported no such changes.

The data obtained in the double-blind, retrospective clinical study suggests that the neuro-nutrients in the composition of the invention are effective in reducing feelings of hunger and therefore in reducing overeating in overweight individuals. The study also indicates that the composition of the invention reduces cravings for sugars and carbohydrates, and leads to an increase in energy levels, stamina, and feelings of well-being.

It was anticipated that the composition of the invention would result in some weight loss. However, the level of weight loss was greater than anticipated. Also, the decrease in cravings for sugar and carbohydrates, and the reported increases in energy and stamina among Group II users were all greater than had been anticipated. The increased feelings of well-being had not been anticipated at all and was quite surprising.

One theory proposed for the effects of one embodiment of the composition of the invention as part of a weight loss regimen is that the effects noted above are due to the ability of the components of the composition of the invention, acting in concert, to correct common cellular deficiencies in the human body that affect a network of bodily functions. Overeating is one effect of the network deficiencies. An effective treatment for these deficiencies requires a number of essential compounds and elements, many of which must be supplemented daily. One embodiment of the composition of the invention supplies a full range of these needed compounds either directly or as a result of the body's digestion of the composition. As noted, phenylalanine is converted to a number of the 14 amino acids the body requires. The enzymes in the one embodiment of the composition of the invention promote the proper digestion and absorption of food by the gastrointestinal tract. L-carnitine and chromium picolinate take specific action in the metabolism of carbohydrates and help the body break down stored fats. The vitamins maintain the body's metabolic levels and the minerals maintain electrolyte levels. The micro nutrients and other ingredients in the composition of the invention act as neurotransmitters to regulate the hypothalamus and other portions of the central nervous system, which in turn regulates the body's autonomous functions including hunger. In the absence of a continuous balanced supply of these compounds that the body requires on a daily basis, functional cell deficiencies cause the hypothalamus to trigger reflex (somatic) hyperperistalsis and metabolic hypoglycemia, which results in a feeling of hunger. The result is overeating in an attempt to provide the nutrients that will repair the functional deficiencies. But overeating without providing the specific needed compounds or needed amino acid links simply results in weight gain without curing the underlying deficiencies.

Thus, one embodiment of the composition of the invention satisfies the central nervous system and eliminates functional cell deficiencies that would otherwise trigger feelings of hunger.

In the preceding detailed description, the invention is described with reference to specific embodiments thereof. It will, however, be evident that various modifications and changes may be made thereto without departing from the broader spirit and scope of the invention as set forth in the claims. The specification and drawings are, accordingly, to be regarded in an illustrative rather than a restrictive sense.

What is claimed is:

1. A dietary supplement composition comprising:
   an effective amount of an appetite suppressant comprising a mixture of effective amounts of DL-phenylalanine, L-glutamine, and St. John's Wort;
   an effective amount of an agent to metabolize fat;
   an effective amount of an anxiety reducer designed to reduce anxiety caused by said appetite suppressant; and
   effective amounts of nutrients in the form of vitamins and minerals.

2. The composition of claim 1, wherein said DL-phenylalanine comprises L-phenylalanine.

3. A dietary supplement composition comprising:
   an effective amount of an appetite suppressant;
   an effective amount of an agent to metabolize fat comprising a mixture of effective amounts of chromium picolinate and L-carnitine;
   an effective amount of an anxiety reducer designed to reduce anxiety caused by said appetite suppressant; and
   effective amounts of nutrients in the form of vitamins and minerals.

4. A dietary supplement composition comprising:
   an effective amount of an appetite suppressant;
   an effective amount of an agent to metabolize fat;
   an effective amount of an anxiety reducer comprising a mixture of effective amounts of St. John's Wort and L-glutamine; and
   effective amounts of nutrients in the form of vitamins and minerals.

5. A dietary supplement composition comprising:
   an effective amount of an appetite suppressant;
   an effective amount of an agent to metabolize fat;
   an effective amount of an anxiety reducer designed to reduce anxiety caused by said appetite suppressant;
   effective amounts of nutrients in the form of vitamins and minerals; and
   an effective amount of digestive enzymes.

6. A dietary supplement composition comprising:
   DL-phenylalanine in an amount of 38% by weight of the total composition;
   L-glutamine in an amount by weight of 6% of the total composition;
   L-tyrosine in an amount by weight of 13% by weight of the total composition;
   L-carnitine in an amount by weight of 3% of the total composition;
   St. John's Wort extract in an amount of 6% by weight of the total composition;
   chromium picolinate in trace amounts by weight of the total composition; and
   a B-complex vitamin in the amount by weight of less than 1.5% of the total composition.

7. The composition of claim 6, wherein the B-complex vitamin includes vitamin B1 in an amount less than 1% by weight of the total composition, vitamin B2 in amount by weight of less than 1% of total composition, vitamin B3 in amount by weight of about 1% of the total composition, vitamin B6 in amount by weight of less than 1% of the total composition, and vitamin B12 in amount by weight of less than 1% of the total composition.

8. The composition of claim 7, further comprising a magnesium salt in an amount by weight of less than 1% of the total composition.

9. The composition of claim 7, further comprising a zinc salt in an amount by weight of less than 1% of the total composition.

10. The composition of claim 7, further comprising a calcium salt in an amount by weight of 11% of the total composition.

11. The composition of claim 7, further comprising:
pepsin in an amount by weight of 2% of the total composition;
bromelain in an amount by weight of 3% of the total composition; and
uva ursi in an amount by weight of 7% of the total composition.

12. The composition of claim 6, further comprising Korean ginseng in an amount by weight of 9% of the total composition.

13. The composition of claim 6, wherein said DL-phenylalanine comprises L-phenylalanine.

14. A method to promote weight loss comprising:
administering a dietary supplement effective amount of a composition including:
DL-phenylalanine in an amount of 38% by weight of the total composition;
L-glutamine in an amount by weight of 6% of the total composition;
L-tyrosine in an amount by weight of 13% by weight of the total composition;
L-carnitine in an amount by weight of 3% of the total composition;
St. John's Wort extract in an amount of 6% by weight of the total composition;
chromium picolinate in trace amounts by weight of the total composition; and
a B-complex vitamin in the amount by weight of less than 1.5% of the total composition.

15. The method of claim 14, wherein said administering step further comprises administering said composition where said DL-phenylalanine of said composition comprises L-phenylalanine.

* * * * *

UNITED STATES PATENT AND TRADEMARK OFFICE
CERTIFICATE OF CORRECTION

PATENT NO.: 5,925,377
DATED       : July 20, 1999
INVENTOR(S): Gerth et al.

It is certified that error appears in the above-identified patent and that said Letters Patent is hereby corrected as shown below:

Column 4, line 44, delete "elf".

In Detailed Description, column 5, lines 20-21, delete "DL- phenylalanine particularly must be phenylalanine" and replace with --DL-phenylalanine, particularly L-phenylalanine, must be--.

Signed and Sealed this

Twenty-seventh Day of June, 2000

Attest:

Q. TODD DICKINSON

*Attesting Officer*     *Director of Patents and Trademarks*